United States Patent [19]

Beck et al.

[11] 4,350,520
[45] Sep. 21, 1982

[54] PLANT GROWTH REGULANT COMPOSITIONS

[75] Inventors: Gunther Beck; Helmut Heitzer, both of Leverkusen; Klaus Lürssen, Bergisch-Gladbach, all of Fed. Rep. of Germany

[73] Assignee: Bayer Aktiengesellschaft, Leverkusen, Fed. Rep. of Germany

[21] Appl. No.: 213,704

[22] Filed: Dec. 5, 1980

[30] Foreign Application Priority Data

Dec. 19, 1979 [DE] Fed. Rep. of Germany ....... 2951201

[51] Int. Cl.$^3$ ............................................. A01N 43/50
[52] U.S. Cl. ...................................... 71/92; 548/343; 544/346
[58] Field of Search ............................ 71/92; 548/343

[56] References Cited

U.S. PATENT DOCUMENTS

| | | | |
|---|---|---|---|
| 4,179,277 | 12/1979 | Beck et al. | 71/92 |
| 4,220,466 | 9/1980 | Patel | 71/92 |
| 4,233,058 | 11/1980 | Sasse et al. | 71/92 |

FOREIGN PATENT DOCUMENTS

| | | | |
|---|---|---|---|
| 750797 | 11/1970 | Belgium | 548/343 |
| 19067 | 11/1980 | European Pat. Off. | |
| 1567084 | of 0000 | Fed. Rep. of Germany | |
| 1921341 | of 0000 | Fed. Rep. of Germany | |

OTHER PUBLICATIONS

Iwasaki, Chem. Abst. 86:106471v.
Iversen et al., Acta Chemica Scandinavica 21, 1967, pp. 279–285.
Papadopoulos, Jour. Org. Chem. vol. 42, No. 24 (1977), pp. 3925–3929.
Dirlam et al. J. Heterocyclic Chem. 17, 409–411 1980.
J. Org. Chem. 42, 3825–3928 (1977).

*Primary Examiner*—Jane T. Fan
*Attorney, Agent, or Firm*—Felfe & Lynch

[57] ABSTRACT

The imidazole-2-carboxylic acid amides of the general formula

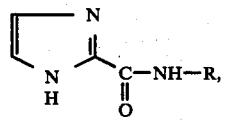

(I)

in which
R represents alkyl, have powerful growth-regulating properties.

The invention provides a method of regulating the growth of plants, which comprises applying to the plants, or to a habitat thereof, a compound of the formula (I) alone or in the form of a composition containing as active ingredient a compound of the formula (I) in admixture with a diluent or carrier.

8 Claims, No Drawings

PLANT GROWTH REGULANT COMPOSITIONS

This invention relates to plant growth regulant compositions and to methods of regulating plant growth. In additional aspect, the invention relates to certain novel imidazole-2-carboxylic acid amide compounds which have plant growth regulant activity.

It is known that certain imidazole-2-carboxylic acid amides can be prepared by reacting imidazole with isocyates (see *J. Org. Chem.* 1977 (42), 3925). Thus, for example, imidazole-2-carboxylic acid n-butylamide is formed in the reaction of imidazole with n-butyl isocyanate in boiling nitro-benzene.

It is also known that certain 4,5-dichloroimidazole-2-carboxylic acid amides have herbicidal properties (see DE-OS German published specification No. 2,610,527). Thus, for example, 4,5-dichloroimidazole-2-carboxylic acid ethylamide can be employed for combating weeds. However, the use of these substances for regulating plant growth has not hitherto been described.

It has now been found that the imidazole-2-carboxylic acid amides of the general formula

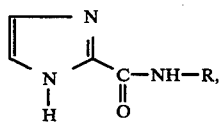
(I)

in which

R represents alkyl, have powerful growth-regulating properties.

Accordingly, the present invention provides a plant growth-regulating composition containing as active ingredient a compound of the formula (I) in admixture with a solid or liquefied gaseous diluent or carrier or in admixture with a liquid diluent or carrier containing a surface-active agent.

The invention also provides a method of regulating the growth of plants, which comprises applying to the plants, or to a habitat thereof, a compound of the formula (I) alone or in the form of a composition containing as active ingredient a compound of the formula (I) in admixture with a diluent or carrier.

Surprisingly, the imidazole-2-carboxylic acid amides of the formula (I) which can be used according to the invention have an outstanding plant growth-regulating action. They can be particularly advantageously employed for promoting growth, especially in the case of sugar beet. The use, according to the invention, of the imidazole-2-carboxylic acid amides of the formula (I) thus represents a valuable enrichment of the art.

The formula (I) provides a general definition of the imidazole-2-carboxylic acid amides which can be used according to the invention. In this formula, R preferably represents straight-chain or branched alkyl with 1 to 18 carbon atoms.

Particularly preferred compounds of the formula (I) are those in which R represents methyl, ethyl, n-propyl, isopropyl, n-butyl, i-butyl, sec.-butyl, tert.-butyl, n-pentyl, neo-pentyl, n-hexyl, n-heptyl, n-octyl, n-decyl, n-dodecyl or n-octadecyl.

Some of the imidazole-2-carboxylic acid amides of the formula (I) which can be used according to the invention are known (see Acta Chem. Scand. 21, 279 (1967) and J. Org. Chem. 1977 (42), 3925).

The compounds of the formula

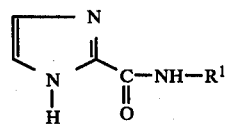
(Ia)

in which $R^1$ represents alkyl, but not n-butyl, are new.

These new substances of the formula (Ia) can be prepared by a process in which (a) imidazole is reacted with isocyanates of the general formula

 $R^1$—NCO (II), in which $R^1$ has the meaning indicated above, in the presence of a diluent, for example nitrobenzene, at temperatures between 150° C. and 250° C., or (b) the dimeric ketene of the formula

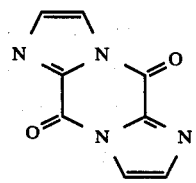
(III)

is reacted with amines of the general formula

 $H_2N$—$R^1$ (IV), in which $R^1$ has the meaning indicated above, if appropriate in the presence of a diluent and if appropriate in the presence of a catalyst, at temperatures between −50° C. and +200° C.

The isocyanates of the formula (II) required as starting substances in process (a) are known.

The dimeric ketene of the formula (III) required as the starting substance in process (b) has not hitherto been described in the literature. It can be prepared by heating imidazole-2-carboxylic acid under reflux with an excess of thionyl chloride, if appropriate in the presence of dimethylformamide as a catalyst.

Imidazole-2-carboxylic acid is known (see Acta Chem. Scand. 21, 279 (1967)).

Possible diluents in the reaction in process (b) are the amines of the formula (IV), used as reactants, themselves—if they are present in the liquid state or melt at low temperatures—and inert organic solvents, such as methylene chloride or chloroform. Furthermore, alcohols with 1 to 4 carbon atoms, such as methanol or isopropanol, or water can also function as diluents.

Catalysts which can be used in process (b) are strong inorganic bases, such as sodium hydroxide or potassium hydroxide, or amines, such as triethylamine or triethylenediamine.

The reaction temperatures can be varied within a substantial range in process (b). In general, the reaction is carried out at temperatures between −50° C. and +200° C., preferably between 0° C. and 100° C.

In carrying out process (b), 2 moles or even a larger excess of amine of the formula (IV) and, if appropriate, 0.01 to 1, preferably 0.1 to 0.5, mole of catalyst are employed per mole of dimeric ketene of the formula (III). The resulting imidazole-2carboxylic acid amides of the formula (I) are isolated by customary methods. In general, a procedure is followed in which, when the reaction has ended, the solvent and/or the component (IV) present in excess is distilled off and, if appropriate, the residue is recrystallised, or sublimed under reduced pressure.

In the formula (Ia), $R^1$ preferably represents straight-chain or branched alkyl with 1 to 18 carbon atoms, but not n-butyl.

The active compounds which can be used according to the invention engage in the metabolism of the plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Promotion of vegetative growth, for example, can be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content is soya or cereals. Using growth regulators it is also possible, for example, to inhibit the degradation of desired constituents, such as, for example, sugar in sugar beet or sugar cane, before or after harvesting.

Using growth regulators, it is furthermore possible to achieve an acceleration of ripening of the harvest product. This is of particular advantage, since it is thereby possible to achieve optimum adaptation to market requirements.

Finally, the resistance of plants to frost, drought or a high salt content in the soil can be induced with growth regulators. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted into the customary formulations, such as solutions, emulsions, suspensions, powders, foams, pastes, granules, aerosols, very fine capsules in polymeric substances and in coating compositions, for use on seed, as well as ULV formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides and herbicides, and also as a mixture with fertilisers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomising, scattering, dusting, foaming and coating. Furthermore it is possible to apply the active compounds in accordance with the ultra-low-volume method, to spread the active compound preparation or the active compound itself on plants or parts of plants or to inject the active compound preparation or the active compound itself into the soil. It is also possible to treat the seeds of plants.

The amounts applied can be varied within a substantial range. In general, 0.01 to 50 kg, preferably 0.05 to 10 kg, of the active compound are employed per hectare of soil surface.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The growth regulating activity of the compounds of this invention is illustrated by the following biotest Example.

In this Example, the compounds according to the present invention are each identified by the number (given in brackets) of the corresponding preparative Example, which will be found later in this specification.

EXAMPLE A

Promotion of growth of sugar beet

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier, and the mixture was made up to the desired concentration with water.

Sugar beet was grown in a greenhouse until formation of the cotyledons was complete. In this stage, the plants were sprayed with the preparations of active compound until dripping wet. After 14 days, the additional growth of the plants was measured and the promotion of growth in percent of the additional growth of the control plants was calculated. 0% promotion of growth denoted a growth which corresponded to that of the control plants. Positive values characterised a promotion of growth in comparison to the control plants.

The test results are given in the following table.

TABLE A

| Active compound | Concentration in ppm | Promotion of growth in % |
| --- | --- | --- |
| (1) | 500 | +5 |
|     | 250 | +5 |
|     | 125 | +15 |
|     | 62.5 | +30 |
|     | 31.25 | +30 |
| (2) | 500 | +20 |
| (3) | 31 | +10 |
| (Control) | — | 0 |

A promotion of growth of young sugar-beet plants leads to a denser crop at an earlier point in time during the vegetation period in the field, which in turn leads to an increase in the yield of sugar-beet.

PREPARATIVE EXAMPLES

EXAMPLE 1

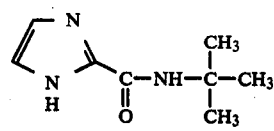

(1)

153 g (2.1 mol) of tert.-butylamine were gradually added to a suspension of 188 g (1 mol) of the dimeric ketene of the formula

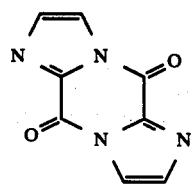

in 1.5 liters of methylene chloride, whereupon the temperature of the reaction mixture rose to the boiling point (about 42° C.). After subsequently stirring the mixture under reflux for one hour, the small amounts of insoluble constituents were filtered off hot and the filtrate was concentrated to dryness in vacuo. Imidazole-2-carboxylic acid tert.-butylamide was thus obtained in virtually quantitative yield. The compound could be sublimed at 100°–120° C./0.01 mm Hg without decomposition and could be crystallised in the form of prisms from water or in the form of long needles from petroleum ether (boiling point: 40°–80° C.). Melting point: 134° C.

PREPARATION OF THE STARTING MATERIAL

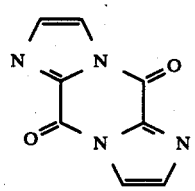

Variant α:

11.2 g (0.1 mol) of imidazole-2-carboxylic acid [which could be prepared, for example, in accordance with the method of J. Am. Chem. Soc., 71, 383 (1949)] were stirred under reflux with 100 ml of thionyl chloride for 5 hours. After cooling the mixture, the solid was filtered off, washed with a little petroleum ether and dried. 5H, 10H-diimidazo[1,2-a:1',2'-d]pyrazine-5,10-dione was thus obtained in virtually quantitative yield in the form of a yellow powder. The substance still did not melt at 290° C. It could be sublimed into yellow crystals at 200°–250° C./0.01 mm Hg without decomposition. IR (KBr): 3137, 1735, 1522, 1445, 1387, 1331, 1274, 1161, 1059, 1018, 810, 800, 748, 699 and 651 cm$^{-1}$.

Variant β:

The procedure followed was as described under (α), with the difference that 1 ml of dimethylformamide was added. As a comparison of the IR spectra showed, the reaction to give the compound of the formula

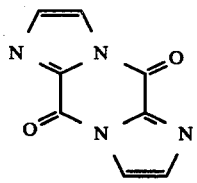

was already virtually complete after about half an hour.

EXAMPLE 2

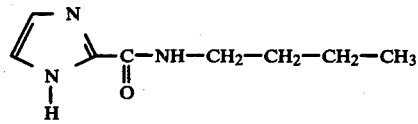

Procedure according to J. Org. Chem. 1977 (42), 3925:

A solution of 0.10 mol of imidazole and 0.10 mol of n-butyl isocyanate in 40 ml of nitrobenzene was heated under reflux for 8 hours. After cooling the reaction mixture, it was diluted with carbon tetrachloride and the solid was filtered off and washed with carbon tetrachloride until the carbon tetrachloride runnings were colourless. After drying, imidazole-2-carboxylic acid n-butylamide was obtained in 18% yield. Melting point: 188°–190° C.

EXAMPLE 3

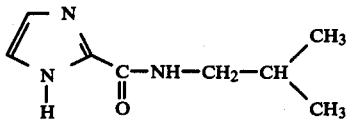

Imidazole-2-carboxylic acid isobutylamide was also prepared by the method described in Example 2, using imidazole and iso-butyl isocyanate as starting materials. Melting point: 202° C.

The compounds listed by means of their formulae in the table below were also prepared by methods analogous to that given in Example 1.

TABLE 1

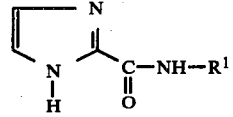

| Example No. | $R^1$ | Melting point in °C. |
|---|---|---|
| 4 | $CH_3$ | 260 (water) |
| 5 | $n\text{-}C_{18}H_{37}$ | 156 (dioxan) |
| 6 | $C_2H_5$ | 210 (water) |
| 7 | $n\text{-}C_3H_7$ | 207 (acetonitrile) |
| 8 | $i\text{-}C_3H_7$ | 226 (acetonitrile) |
| 9 | $-CH_2-C(CH_3)_3$ | 184 (acetonitrile) |
| 10 | sec. $-C_4H_9$ | 209 (acetonitrile) |
| 11 | $n\text{-}C_6H_{13}$ | 194 (acetonitrile) |
| 12 | $-CH_2-CH(C_2H_5)-CH_2-CH_2-C_2H_5$ | 154 (dioxane) |
| 13 | $n\text{-}C_{12}H_{25}$ | 165 (dioxane) |
| 14 | $n\text{-}C_{14}H_{29}$ | 165 (acetonitrile) |
| 15 | $n\text{-}C_{16}H_{33}$ | 158 (dioxane) |

It will be understood that the specification and examples are illustrative but not limitative of the present invention and that other embodiments within the spirit and scope of the invention will suggest themselves to those skilled in the art.

What is claimed is:

1. Method of promoting the growth of sugar beets, which method comprises applying to the plants or their habitat an effective amount of an imidazole-2-carboxylic acid amide compound of the formula

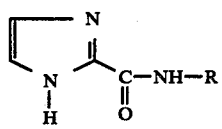

wherein R is alkyl with 1 to 18 carbon atoms.

2. Method as claimed in claim 1 wherein said compound is imidazole-2-carboxylic acid tert.-butylamide.

3. Method as claimed in claim 1 wherein said compound is imidazole-2-carboxylic acid n-butylamide.

4. Method as claimed in claim 1 wherein said compound is imidazole-2-carboxylic acid iso-butylamide.

5. Method as claimed in claim 1 wherein said compound is imidazole-2-carboxylic acid methylamide.

6. Method as claimed in claim 1 wherein said compound is imidazole-2-carboxylic acid n-propylamide.

7. Method as claimed in claim 1 wherein the said compound is applied to an area of agriculture in an amount of 0.01 to 50 kg per hectare.

8. Method as claimed in claim 1 wherein said compound is applied to an area of agriculture in an amount of 0.05 to 10 kg per hectare.

* * * * *